US012262904B2

(12) United States Patent
Steketee et al.

(10) Patent No.: US 12,262,904 B2
(45) Date of Patent: Apr. 1, 2025

(54) SURGICAL INSTRUMENT AND RELATED METHODS

(71) Applicant: BOLDER SURGICAL, LLC, Louisville, CO (US)

(72) Inventors: Nathan Steketee, Louisville, CO (US); Joseph Bucciaglia, Boulder, CO (US)

(73) Assignee: Bolder Surgical, LLC, Louisville, CO (US)

( * ) Notice: Subject to any disclaimer, the term of this patent is extended or adjusted under 35 U.S.C. 154(b) by 881 days.

(21) Appl. No.: 17/047,105

(22) PCT Filed: May 11, 2019

(86) PCT No.: PCT/US2019/031900
§ 371 (c)(1),
(2) Date: Oct. 13, 2020

(87) PCT Pub. No.: WO2019/217945
PCT Pub. Date: Nov. 14, 2019

(65) Prior Publication Data
US 2021/0393282 A1 Dec. 23, 2021

Related U.S. Application Data

(60) Provisional application No. 62/670,193, filed on May 11, 2018.

(51) Int. Cl.
*A61B 17/29* (2006.01)
*A61B 17/072* (2006.01)
*A61B 17/295* (2006.01)

(52) U.S. Cl.
CPC ............ *A61B 17/29* (2013.01); *A61B 17/072* (2013.01); *A61B 17/295* (2013.01); *A61B 2017/2936* (2013.01)

(58) Field of Classification Search
CPC .............................................. A61B 2017/2944
See application file for complete search history.

(56) References Cited

U.S. PATENT DOCUMENTS 5,471,992 A * 12/1995 Banik ................ A61B 10/0266
600/564
5,673,841 A 10/1997 Schulze et al.
(Continued)

FOREIGN PATENT DOCUMENTS

EP 0717959 A2 6/1996
EP 2517635 10/2012
(Continued)

OTHER PUBLICATIONS

Kim, Yeonkyung. International Search Report and Written Opinion for PCT/US2019/031900, mailed Sep. 25, 2019, 10 pages, published in: Korea.
(Continued)

*Primary Examiner* — Shaun L David
(74) *Attorney, Agent, or Firm* — Vista IP Law Group, LLP

(57) ABSTRACT

A surgical instrument and related methods are disclosed. The instrument has a first jaw, a second jaw, and a first actuator. The first actuator has a cam mechanism to engage the first jaw to effectuate movement of the first jaw between an open position, a clamping position, and a closed position. Movement of the first jaw between the open position and the clamping position includes a rotational component. Movement of the first jaw between the clamping position and the closed position is translational.

21 Claims, 5 Drawing Sheets

(56) References Cited

U.S. PATENT DOCUMENTS

| | | |
|---|---|---|
| 9,839,429 B2 | 12/2017 | Weisenburgh, II et al. |
| 2004/0193197 A1 | 9/2004 | Vidal |
| 2012/0089158 A1* | 4/2012 | Martinez ............ A61B 17/2816 606/142 |
| 2014/0239036 A1* | 8/2014 | Zerkle .................. A61B 17/068 227/175.1 |
| 2014/0367447 A1 | 12/2014 | Woodard, Jr. et al. |
| 2016/0345971 A1 | 12/2016 | Bucciaglia et al. |
| 2018/0110513 A1 | 4/2018 | Baxter, III et al. |

FOREIGN PATENT DOCUMENTS

| | | |
|---|---|---|
| EP | 2772201 A2 | 9/2014 |
| JP | H8-336540 | 12/1996 |
| JP | 2016-508416 | 3/2016 |
| WO | WO2014133774 A2 | 9/2014 |
| WO | WO2016182933 A1 | 11/2016 |
| WO | 2019/217945 A1 | 11/2019 |

OTHER PUBLICATIONS

Foreign OA for JP Patent Appln. No. 2020-560963 dated Feb. 17, 2023 (with English translation).
Extended European Search Report for EP Patent Appln. No. 19799733.1 dated Jan. 4, 2022.
Foreign Response to EESR for EP Patent Appln. No. 19799733.1 dated Jul. 21, 2022.
Foreign Exam Report EP Patent Appln. No. 19799733.1 dated Mar. 20, 2024.

* cited by examiner

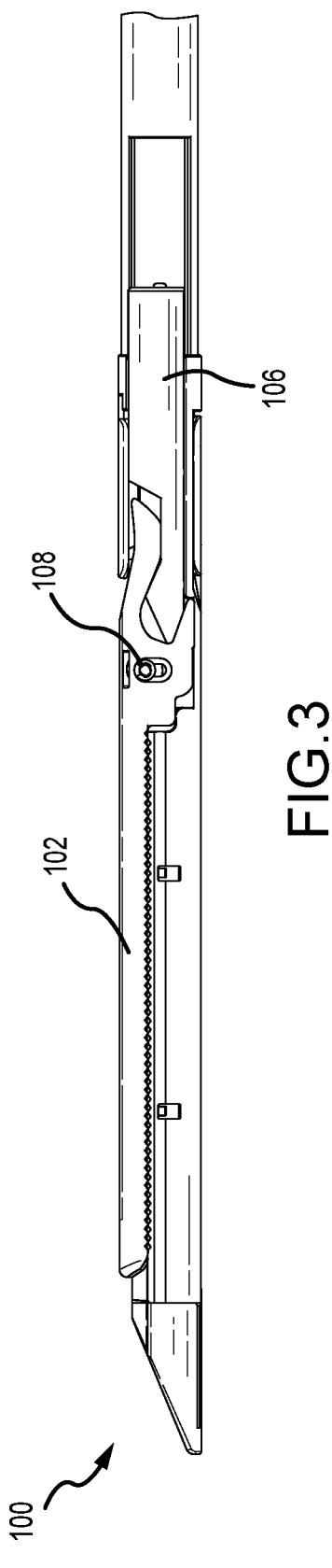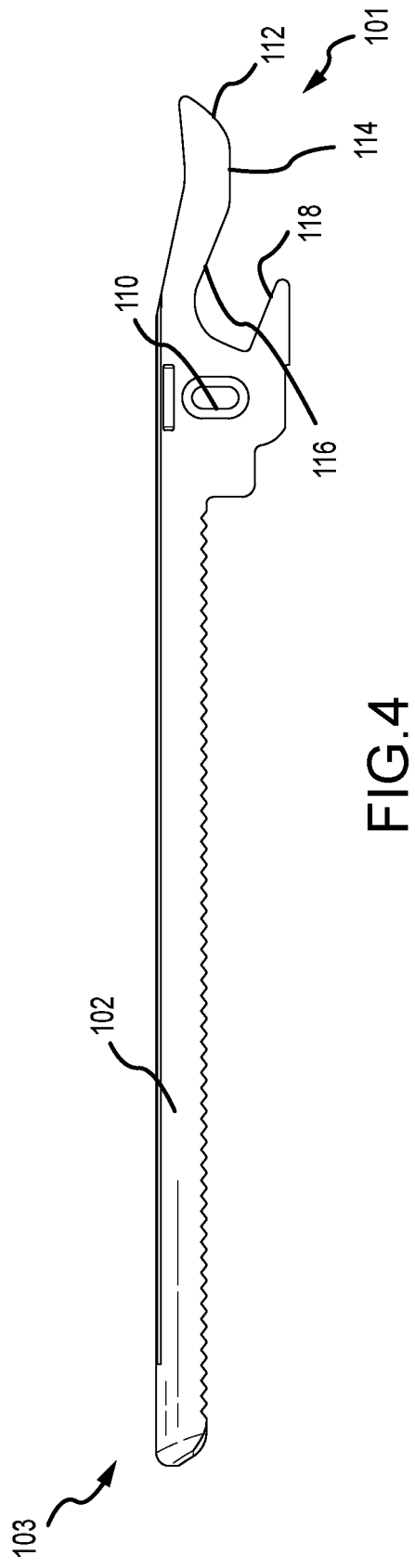

SURGICAL INSTRUMENT AND RELATED METHODS

CROSS-REFERENCE TO RELATED APPLICATIONS

This application claims priority to U.S. Provisional Application No. 62/670,193, filed May 11, 2018 and entitled "Surgical Instrument and Related Methods," the entire disclosure of which is hereby incorporated by reference for all proper purposes.

FIELD

The present invention relates generally to surgical instruments, and more specifically to actuators for surgical instruments.

BACKGROUND

There is a need for an improved actuator for a surgical instrument, particularly for small instruments, such as, for example, surgical stapling instruments of around 5 millimeters in diameter or less, as well as other new and useful improvements.

SUMMARY

An exemplary surgical instrument has a first jaw, a second jaw, and a first actuator. The first actuator has a cam mechanism to engage the first jaw to effectuate movement of the first jaw between an open position, a clamping position, and a closed position. Movement of the first jaw between the open position and the clamping position includes a rotational component. Movement of the first jaw between the clamping position and the closed position is translational.

An exemplary method of using a surgical instrument includes moving a first actuator between a first position and a second position distal of the first position to effectuate movement of the first jaw between an open position and a clamping position. The exemplary method includes moving the first actuator between the second position and a third position distal of the second position to effectuate movement of the first jaw between the clamping position and a closed position. Movement of the first jaw between the open position and the clamping position includes a rotational component. Movement of the first jaw between the clamping position and the closed position is translational.

BRIEF DESCRIPTION OF THE DRAWINGS

FIG. 3. illustrates a side view of the end effector in FIG. 1 in a closed position;

FIG. 4. illustrates a side view of the first jaw of the end effector in FIG. 1;

DETAILED DESCRIPTION

Figure 1:
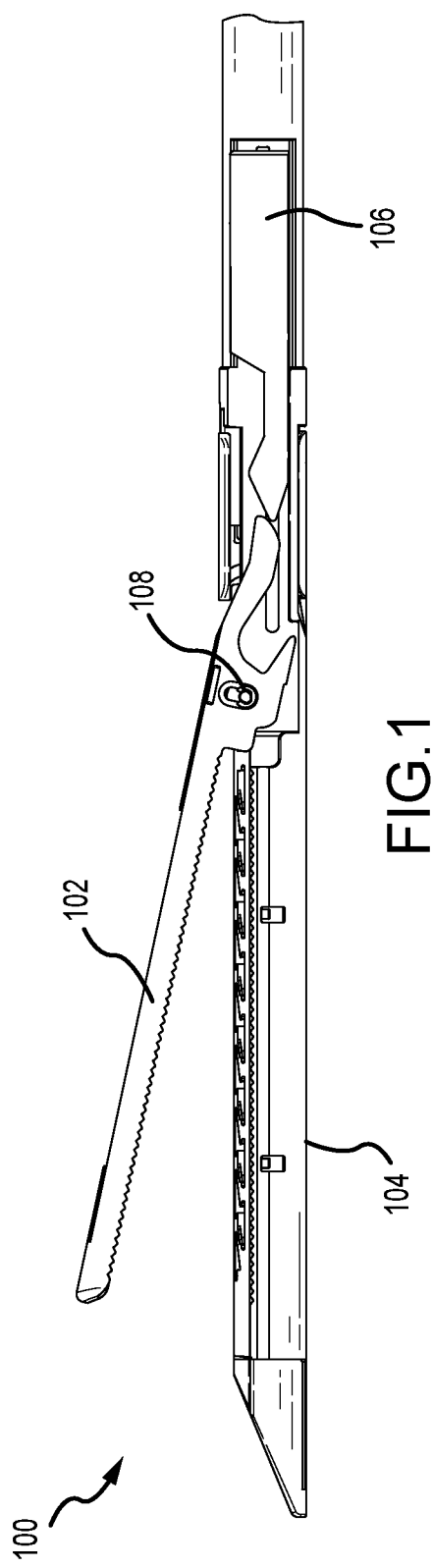
FIG. 1. illustrates a side view of an exemplary end effector with a first jaw in an open position.
Figure 2:
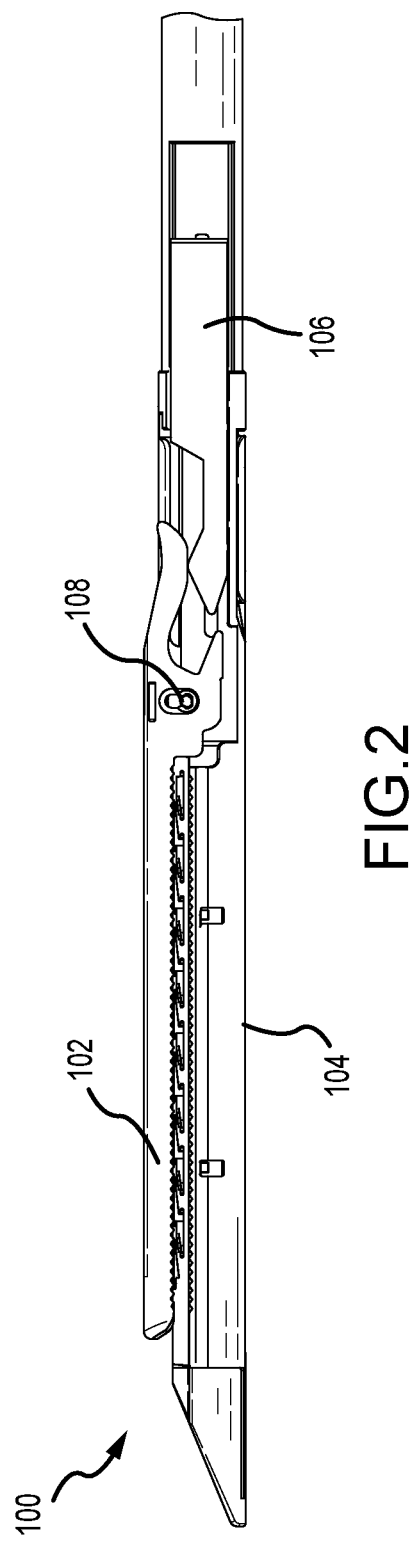
FIG. 2. illustrates a side view of the end effector in FIG. 1 in a clamping position.

Turning to FIGS. 1-3, an exemplary end effector 100 for a surgical instrument is described. The end effector 100 may be referenced herein as surgical instrument 100. The surgical instrument may be a surgical stapler, although those skilled in the art will recognize that the teachings herein are suitable to other instruments, in particular endo-surgical sealers or other surgical instruments requiring precision grasping and clamping of tissue in a confined space.

As illustrated, the surgical instrument 100 has an upper or first jaw or anvil 102 and a lower or second jaw 104, which may also be referenced herein as a cartridge holder or cartridge housing 104. The instrument 100 may have an actuator 106 configured to engage the upper jaw 102 to effectuate movement of the upper jaw between an open position (see e.g. FIG. 1), a clamping position (see e.g. FIG. 2), and/or a closed position (see e.g. FIG. 3). For the purpose of this document, the term "clamping position" shall be understood to mean a position wherein the upper jaw and the lower jaw are positioned near or approximate to one another for effectuating an action on tissue positioned between the jaws. The term "closed position" shall be understood to mean a position wherein the upper jaw and the lower jaw are positioned closer together than in the clamping position, and in some embodiments may be in contact with each other at one or more locations along a tissue interaction area of the jaws. The term "open position" shall be understood to mean a position wherein at least a distal portion of the jaws are farther apart from each other than they are in the clamping position or wherein the jaws are rotated away from each other.

The actuator 106 may be configured to move or translate in a longitudinal direction, wherein longitudinal movement of the actuator effectuates rotation of the upper jaw between the open position and the clamping position and linear translation of the upper jaw between the clamping position and the closed position. FIG. 1 illustrates the actuator 106 in a proximal position relative to the second jaw 104 and/or first jaw 102. FIG. 2 illustrates the actuator 106 in a second position that is distal of the proximal position shown in FIG. 1. FIG. 3 illustrates the actuator 106 in a third position which is distal of both positions illustrated in FIG. 1 and FIG. 2.

In some examples, the instrument 100 includes a multi-positional cam system having: (a) anvil 102, (b) actuator 106, (c) housing 104 with pivot member or pivot pin 108 and actuator guide slot 126, and (d) spring member.

In some examples, a surgical instrument has an upper jaw, which may be an anvil for a surgical stapler, a lower jaw, which may be a cartridge housing, and a first actuator. The first actuator may have a cam configured to effectuate movement of the upper jaw between an open position, a clamping position, and a closed position. Movement of the upper jaw between the open position and the clamping position may include a rotational and translational component. In some embodiments, movement of the upper jaw between the open position and the clamping position is strictly rotational. Movement of the upper jaw between the clamping position and the closed position may be substantially translational, with little to no rotational component. In some embodiments, movement of the upper jaw between the clamping position and the closed position is strictly translational.

Figure 5:
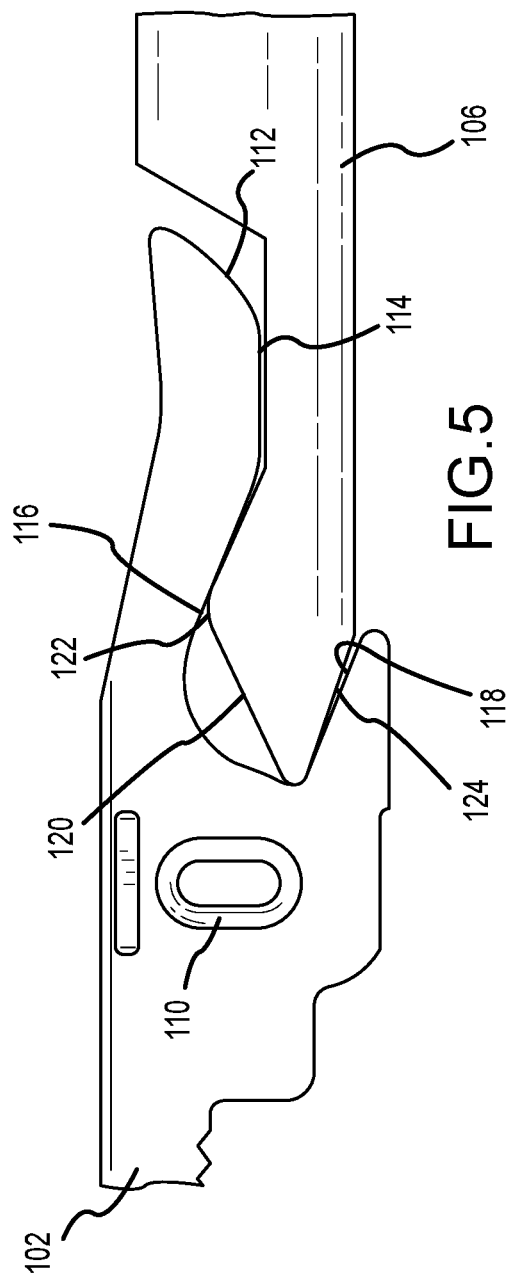
FIG. 5. illustrates a detailed side view of the first jaw and the first actuator of the end effector in FIG. 1.

The first actuator 106 may have a cam mechanism with a plurality of camming surfaces to engage a plurality of surfaces on the upper jaw to effectuate a desired movement of the upper jaw. As shown in FIGS. 4-5, the cam mechanism may have a first cam surface 120, a second cam surface 124, and a third cam surface 122. The upper jaw 102 may have a first jaw surface 112, a second jaw surface 118, and a third jaw surface 116, the second jaw surface 118 positioned distal of the first and third jaw surfaces 112, 116, and the first jaw surface 112 positioned proximal of the second and third jaw surfaces 118, 116.

As illustrated in FIG. 1 and FIG. 2, the first cam surface 120 may be configured to engage the first jaw surface 112 as the first actuator 106 is moved distally from a first position to a second position to effectuate rotation of the upper jaw 102 from the open position to the clamping position.

As illustrated in FIG. 3, the second cam surface 124 may be configured to engage the second jaw surface 118 as the first actuator 106 is moved distally from the second position to a third position to effectuate translation of the upper jaw 102 from the clamping position to the closed position.

As one can also appreciate from FIG. 3, the third cam surface 122 may be configured to engage the third jaw surface 116 as the first actuator 106 moves proximally from the third position to a fourth position to effectuate translation of the upper jaw 102 from the closed position to the clamping position.

Continuing with FIGS. 1-3, a pin may be positioned on one of the upper jaw or the lower jaw, and an elongated slot may be positioned on the other one of the upper jaw or the lower jaw. The pin and elongated slot are configured to allow a pivot axis of the upper jaw to translate between a first position and a second position.

The instrument may include a second actuator that is substantially identical to the first actuation and positioned on an opposing side of the longitudinal axis of the instrument. A translating member may be positioned between the first actuator and the second actuator. The translating member may include a cutting mechanism and/or a clamping member such as an expanding I-beam as described in co-owned US Pat. Pub. No. 2016/0345971 A1, entitled Surgical Stapler, published on Dec. 1, 2016, the entire disclosure of which is hereby incorporated by reference for all proper purposes.

Although not illustrated, the instrument may include a biasing mechanism to bias the instrument towards the open position or the closed position. Those skilled in the art will recognize that there are many means for providing a biasing mechanism or feature, including, but not limited to, springs, magnets, low durometer polymers, etc. In some embodiments, the biasing mechanism is configured to apply a translational force to the upper jaw, such as to bias the upper jaw or anvil from the closed position to the clamping position, or vice versa. In some embodiments, the biasing mechanism is configured to apply a rotational force to the upper jaw, such as to bias the upper jaw or anvil from the clamping position towards the open position, or vice versa. In some embodiments, the biasing mechanism is configured to apply a force tending to translate and rotate the upper jaw or anvil.

In some embodiments, the biasing mechanism is configured to bias a lower surface of the elongated slot against the pivot pin (see e.g. FIG. 2). In some embodiments, the upper jaw is moved between the clamping position and the open position while the lower surface is maintained in contact with the pivot pin. In some embodiments, the actuator is configured to cause an upper surface of the elongated slot to contact the pivot pin (see e.g. FIG. 3).

In some embodiments, the instrument described herein reduces the degrees of freedom in the system and provides an optimized geometry for maximum component strength. That is, when moving between the open configuration and the clamping configuration, the jaws are limited to relative rotational movement. In some embodiments, a biasing mechanism and an actuator as described herein may effectuate this movement. When moving between the closed position and the clamping configuration, the jaws are limited to relative translational movement. In some embodiments, a biasing mechanism and an actuator as described herein may effectuate this movement.

Turning now to FIG. 4, in some embodiments, the second and third cam surfaces of the upper jaw may be parallel to each other.

As illustrated in FIG. 5, in some embodiments, the second and third cam surfaces 124, 122 of the upper jaw 102 may be in contact with the actuator 106 simultaneously when moving between the clamping position and closed position. Having two contact points supports in limiting movement of the upper jaw 102 or anvil to translational movement between the clamping position and the closed position, and/or may improve the structural integrity of the instrument. In some embodiments, a biasing mechanism may tend to rotationally open the jaws, while contact at two cam surfaces on the upper jaw or anvil effectuates translational movement and counteracts the tendency of the upper jaw 102 or anvil to rotate.

Figure 6:
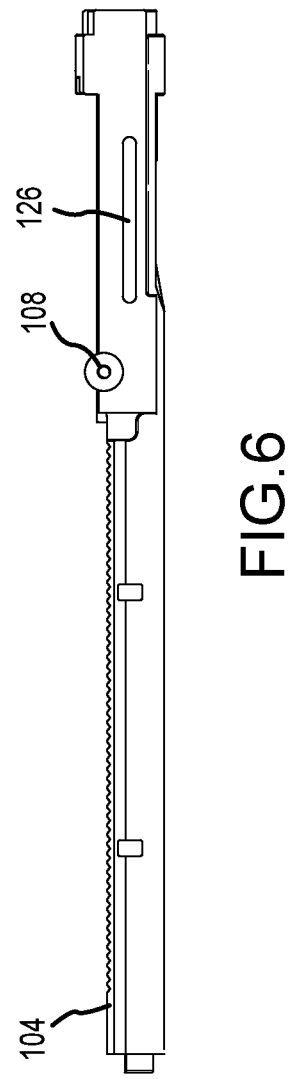
FIG. 6. illustrates a side view of a portion of the second jaw of the end effector in FIG. 1.
Figure 7:
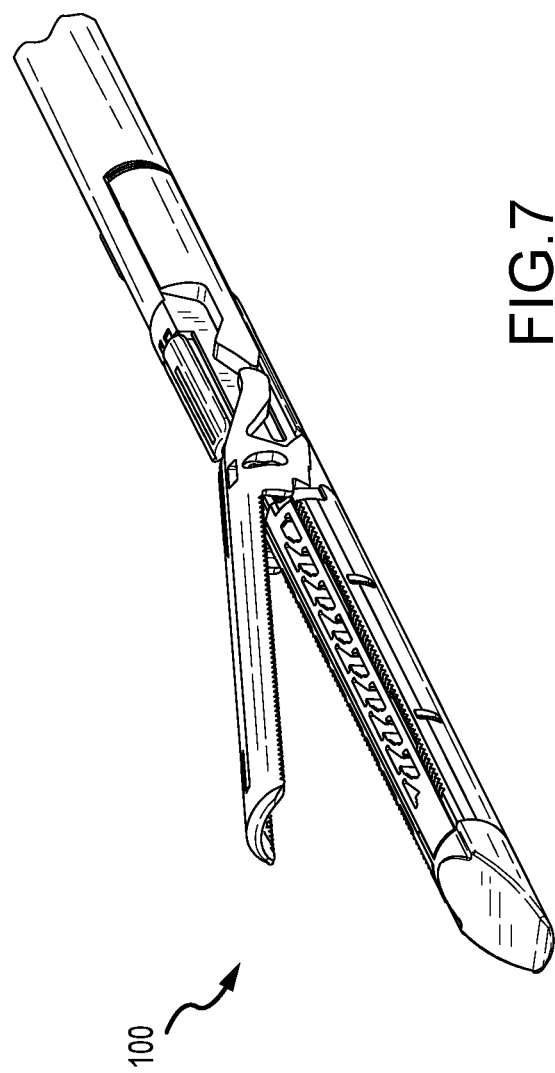
FIG. 7 illustrates a perspective view of the end effector in FIG. 1.

As illustrated in FIG. 6, the housing may include one or more flange surfaces for engaging a projection on the actuator to support the distal end of the actuator, thereby improving the structural integrity of the instrument while still allowing for a small structure.

As illustrated in FIGS. 1-3, in some embodiments, the upper jaw or anvil is limited to translational movement unless a pre-selected pivot axis of the upper jaw or anvil is aligned with a defined transverse axis of the lower jaw, cartridge, or housing.

Continuing with FIGS. 1-3, in some embodiments, one or more of the first, second, and third cam surfaces on the upper jaw or anvil are positioned proximal of and lower than the pre-selected pivot axis. In some embodiments, each of the first, second, and third cam surfaces of the upper jaw or anvil are positioned proximal of and lower than the pre-selected pivot axis.

Figure 8:
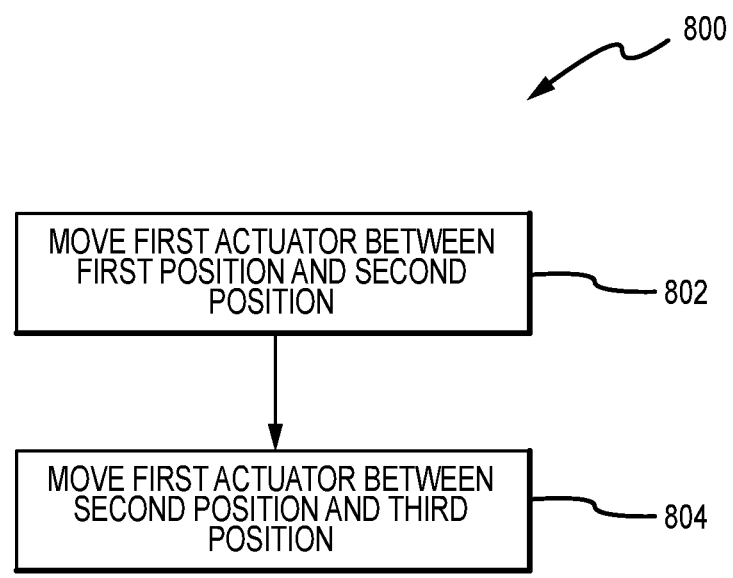
FIG. 8 is a flowchart of an exemplary method.

Turning now to FIG. 8, an exemplary method 800 is described. A method 800 of using a surgical instrument having a first jaw, a second jaw, and a first actuator having a cam mechanism to engage the first jaw may include moving 802 the first actuator between a first position and a second position distal of the first position to effectuate movement of the first jaw between an open position and a clamping position. The method 800 may include moving 804 the first actuator between the second position and a third position distal of the second position to effectuate movement of the first jaw between the clamping position and a closed position. Movement of the first jaw between the open position and the clamping position is rotational in some embodiments. Movement of the first jaw between the clamping position and the closed position is translational in some embodiments.

Moving the first actuator may consist of translating the first actuator.

In some embodiments, the cam mechanism has a first cam surface 120, a second cam surface 124, and a third cam surface 122. In some embodiments, the first jaw has a first jaw surface 112, a second jaw surface 118, and a third jaw surface 116, the second jaw surface 118 positioned distal of the first and third jaw surfaces 112, 116, and the first jaw surface 112 positioned proximal of the second and third jaw surfaces. In some embodiments, the moving the first actuator causes the first cam surface is 120 to engage the first jaw surface 112 as the first actuator is moved distally from the first position to the second to effectuate rotation of the first jaw from the open position to the clamping position. The moving the first actuator may cause the second cam surface 124 to engage the second jaw surface 118 as the first actuator is moved distally from the second position to the third position to effectuate translation of the first jaw from the clamping position to the closed position. The moving the first actuator may cause the third cam surface 122 to engage the third jaw surface 116 as the first actuator is moved proximally from the third position to effectuate translation of the first jaw from the closed position to the clamping position.

Some embodiments of the method 800 may include biasing the first jaw towards the open position.

Some embodiments of the method 800 may include causing a pivot axis of the first jaw to move between a first position and a second position different from the first position.

Some embodiments of the method may include using a second actuator to effectuate movement of a translating member positioned between the first actuator and the second actuator.

Each of the various elements disclosed herein may be achieved in a variety of manners. This disclosure should be understood to encompass each such variation, be it a variation of an embodiment of any apparatus embodiment, a method or process embodiment, or even merely a variation of any element of these. Particularly, it should be understood that the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled.

As but one example, it should be understood that all action may be expressed as a means for taking that action or as an element which causes that action. Similarly, each physical element disclosed should be understood to encompass a disclosure of the action which that physical element facilitates. Regarding this last aspect, by way of example only, the disclosure of an actuator should be understood to encompass disclosure of the act of actuating—whether explicitly discussed or not—and, conversely, were there only disclosure of the act of actuating, such a disclosure should be understood to encompass disclosure of an "actuating mechanism". Such changes and alternative terms are to be understood to be explicitly included in the description.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A surgical instrument comprising:
a first jaw;
a second jaw; and
a first actuator having a cam mechanism configured to engage the first jaw to effectuate movement of the first jaw relative to the second jaw between an open position and a clamping position, and to effectuate movement of the first jaw relative to the second jaw between the clamping position and a closed position;
wherein the movement of the first jaw relative to the second jaw between the open position and the clamping position includes a rotational component; and
wherein the movement of the first jaw relative to the second jaw between the clamping position and the closed position is strictly translational;
wherein:
the cam mechanism has a first cam surface, a second cam surface, and a third cam surface;
the first jaw comprises a first jaw surface, a second jaw surface, and a third jaw surface, the second jaw surface positioned distal of the first and third jaw surfaces, and the first jaw surface positioned proximal of the second and third jaw surfaces; wherein
the first cam surface is configured to engage the first jaw surface as the first actuator is moved distally from a first position to a second position to effectuate rotation of the first jaw from the open position to the clamping position;
the second cam surface is configured to engage the second jaw surface as the first actuator is moved distally from the second position to a third position to effectuate translation of the first jaw from the clamping position to the closed position; and
the third cam surface is configured to engage the third jaw surface as the first actuator is moved proximally to effectuate strict translation of the first jaw from the closed position to the clamping position.

2. The surgical instrument of claim 1, further comprising:
a biasing mechanism configured to bias the first jaw towards the open position.

3. The surgical instrument of claim 2, wherein:
the biasing mechanism is configured to apply a translational force to the first jaw.

4. The surgical instrument of claim 2, wherein:
the biasing mechanism is configured to apply a rotational force to the first jaw.

5. The surgical instrument of claim 1, further comprising:
a second actuator; and
a translating member positioned between the first actuator and the second actuator.

6. The surgical instrument of claim 5, wherein:
the translating member comprises a cutting mechanism.

7. The surgical instrument of claim 1, wherein:
the movement of the first jaw between the open position and the clamping position includes a translational component.

8. The surgical instrument of claim 1, wherein the movement of the first jaw between the clamping position and the closed position is translational in a direction that is perpendicular to a longitudinal axis of the surgical instrument.

9. The surgical instrument of claim 1, wherein when the first jaw is in the closed position, the first jaw is closer to the second jaw compared to when the first jaw is in the clamping position.

10. A surgical instrument comprising:
a first jaw;
a second jaw;
a pin at one of the first jaw or the second jaw; and
an elongated slot positioned on the other one of the first jaw or the second jaw; and
a first actuator having a cam mechanism configured to engage the first jaw to effectuate movement of the first jaw relative to the second jaw between an open position and a clamping position, and to effectuate movement of the first jaw relative to the second jaw between the clamping position and a closed position;
wherein the movement of the first jaw relative to the second jaw between the open position and the clamping position includes a rotational component; and
wherein the movement of the first jaw relative to the second jaw between the clamping position and the closed position is strictly translational;
wherein the pin and elongated slot are configured to allow a pivot axis of the first jaw to translate between a first position and a second position different from the first position; and
wherein the cam mechanism has a cam surface configured to engage with a jaw surface of the first jaw, and wherein the pin is distal to the jaw surface of the first jaw, and is distal to the cam surface of the cam mechanism.

11. The surgical instrument of claim 10, further comprising a biasing mechanism configured to bias the first jaw towards the open position.

12. The surgical instrument of claim 10, further comprising:
a second actuator; and
a translating member positioned between the first actuator and the second actuator.

13. The surgical instrument of claim 12, wherein the translating member comprises a cutting mechanism.

14. A surgical instrument comprising:
a first jaw;
a second jaw; and
a first actuator having a cam mechanism configured to engage the first jaw to effectuate movement of the first jaw relative to the second jaw between an open position and a clamping position, and to effectuate movement of the first jaw relative to the second jaw between the clamping position and a closed position;
wherein the movement of the first jaw relative to the second jaw between the clamping position and the closed position is strictly translational;
wherein the surgical instrument also comprises a pin at the first jaw or the second jaw; and
wherein the cam mechanism has a cam surface configured to engage with a jaw surface of the first jaw, and wherein the pin is distal to the jaw surface of the first jaw, and is distal to the cam surface of the cam mechanism.

15. The surgical instrument of claim 14, wherein:
the first actuator is configured to translate.

16. The surgical instrument of claim 14, further comprising: a biasing mechanism configured to bias the first jaw towards the open position.

17. The surgical instrument of claim 14, further wherein a pivot axis of the first jaw is configured to move between a first position and a second position different from the first position.

18. The surgical instrument of claim 14, further comprising a second actuator configured to effectuate movement of a translating member positioned between the first actuator and the second actuator.

19. The surgical instrument of claim 14, wherein: the movement of the first jaw between the open position and the clamping position includes a translational component.

20. The surgical instrument of claim 14, wherein the movement of the first jaw between the clamping position and the closed position is strictly translational in a direction that is perpendicular to a longitudinal axis of the surgical instrument.

21. The surgical instrument of claim 14, wherein when the first jaw is in the closed position, the first jaw is closer to the second jaw compared to when the first jaw is in the clamping position.

* * * * *